United States Patent [19]

Schwarzmaier et al.

[11] Patent Number: 4,747,914

[45] Date of Patent: May 31, 1988

[54] PROCESS FOR THE PURIFICATION OF 1,2-DICHLOROETHANE

[75] Inventors: Peter Schwarzmaier, Kastl; Walter Fröhlich, Burgkirchen; Wenzel Kühn, Burgkirchen; Josef Riedl, Burgkirchen; Iwo Schaffelhofer, Burghausen; Erich Mittermaier, Tüssling; Reinhard Krumböck, Burgkirchen, all of Fed. Rep. of Germany

[73] Assignee: Hoechst Aktiengesellschaft, Frankfurt am Main, Fed. Rep. of Germany

[21] Appl. No.: 867,809

[22] Filed: May 27, 1986

[30] Foreign Application Priority Data

May 29, 1985 [DE] Fed. Rep. of Germany ....... 3519161

[51] Int. Cl.$^4$ .................... B01D 3/14; C07C 17/38
[52] U.S. Cl. .................................. 203/22; 203/25; 203/29; 203/73; 203/87; 203/DIG. 9; 570/216; 570/262
[58] Field of Search ............... 570/262; 203/73, 77, 203/29, 38, 49, 87, 25, 27, DIG. 9, 22

[56] References Cited

U.S. PATENT DOCUMENTS

| | | | |
|---|---|---|---|
| 2,900,312 | 8/1959 | Gilmore | 203/2 |
| 3,634,200 | 1/1972 | Obrecht et al. | 570/262 |
| 3,963,584 | 6/1976 | Tsao | 570/262 |
| 4,060,460 | 11/1977 | Smalley et al. | 570/262 |
| 4,257,850 | 3/1981 | Rechmeier et al. | 203/29 |
| 4,306,942 | 12/1981 | Brush et al. | 203/DIG. 9 |
| 4,347,391 | 8/1982 | Campbell | 570/252 |
| 4,351,976 | 9/1982 | Ariki et al. | 570/262 |
| 4,421,607 | 12/1983 | Ogura et al. | 203/DIG. 9 |
| 4,484,985 | 11/1984 | Bannon | 203/87 |
| 4,555,311 | 11/1985 | Ward | 203/25 |

FOREIGN PATENT DOCUMENTS

| | | |
|---|---|---|
| 1189057 | 6/1985 | Canada . |
| 1204787 | 5/1986 | Canada . |
| 0026349 | 9/1980 | European Pat. Off. . |
| 0082342 | 6/1983 | European Pat. Off. . |
| 0131932 | 1/1985 | European Pat. Off. . |
| 1959211 | 6/1970 | Fed. Rep. of Germany ...... 570/262 |
| 2427045 | 1/1975 | Fed. Rep. of Germany . |
| 2935884 | 4/1981 | Fed. Rep. of Germany . |
| 3137513 | 4/1983 | Fed. Rep. of Germany . |

Primary Examiner—Wilbur Bascomb
Attorney, Agent, or Firm—Curtis, Morris & Safford

[57] ABSTRACT

A process for the purification of 1,2-dichloroethane is described, in which the crude product, containing not more than 3% by weight of high-boilers, is distilled in a first column at 125° to 180° C. in such a way that the bottom product contains not more than 7% by weight of high-boilers. The purified, vaporous 1,2-dichloroethane discharged at the head of this column is used to heat product streams containing 1,2-dichloroethane. The bottom product from the first column is distilled in a second column, advantageously at a pressure of 5 to 40 kPa, together with a feed composed of vaporous 1,2-dichloroethane obtained from the reaction of ethylene with chlorine. The process makes it possible to purify 1,2-dichloroethane with a saving in energy.

5 Claims, 1 Drawing Sheet

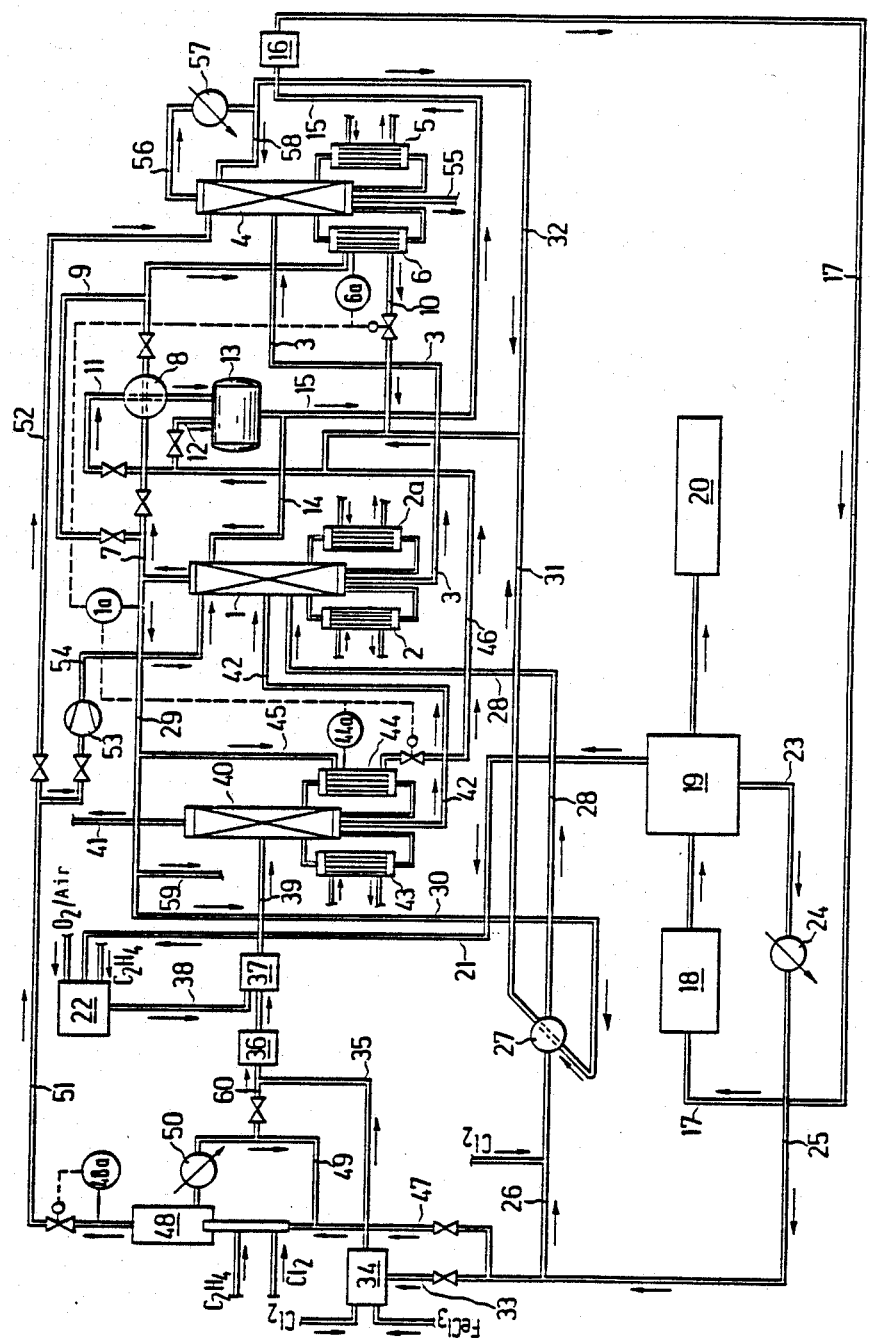

PROCESS FOR THE PURIFICATION OF 1,2-DICHLOROETHANE

The invention relates to a process for the purification of 1,2-dichloroethane by distillation, adjusting the head temperature of the distillation column to 125° to 180° C., taking off at the head of this column vaporous 1,2-dichloroethane, passing it through at least one heat exchanger and then recycling part of said 1,2dichloroethane in liquid form to said column and removing part of said 1,2-dichloroethane as purified product.

1,2-Dichloroethane is produced in large quantities. The bulk of this is subjected to thermal cracking, in the course of which vinyl chloride and hydrogen chloride are formed. The 1,2-dichloroethane must have a high degree of purity for this thermal cracking. Usually, only part of the 1,2-dichloroethane is thermally cracked; a considerable part remains unchanged and is recycled to the cracking reaction after being purified from the by-products of cracking. In this process, the reacted part of the 1,2-dichloroethane is continually replaced by freshly prepared product. The reactions used for the abovementioned preparation are, approximately, in each case up to one half the reaction of ethylene with chlorine (described below as "direct chlorination") and the reaction of ethylene with hydrogen chloride and oxygen (described below as "oxychlorination"). Depending on its particular origin, the 1,2-dichloroethane contains various impurities, which, as a rule, are removed by three different purification stages.

1. Removing the water and the low-boilers by distillation,
2. removing the bulk of the 1,2-dichloroethane by distillation, and
3. removing the residual amount of 1,2-dichloroethane by distillation, the high-boilers remaining in the bottom product. Whereas the distillation columns for 1 and 2 are usually operated under normal atmospheric pressure, reduced pressure is used in the case of 3.

Frequently the 1,2-dichloroethane which is circulated is also pretreated with chemical agents (for example chlorine) before distillation.

In order to carry out the purification of the 1,2-dichloroethane as economically as possible, it is desirable to use processes which enable the energy produced or to be applied to be utilized to the best possible extent. A process is known for this purpose in which ethylene is reacted with chlorine in a circulating medium, preferably 1,2-dichloroethane, under pressure and at a temperature below the vaporization temperature of 1,2-dichloroethane, and the reaction mixture is conveyed into a zone at a lower pressure. In this zone, part of the 1,2-dichloroethane is vaporized, purified via a rectifying zone and removed, while the remainder of the 1,2-dichloroethane is recycled. The 1,2-dichloroethane is thus purified by means of the heat formed in the reaction between ethylene and chlorine.

Another known process is operated in a similar manner, pressures of 0.3 to 1.3 bar and temperatures of 50° to 90° C. being used, and part of the chlorine being dissolved in the reaction product. Before the chlorine is dissolved, ortho-cresol or meta-cresol or monochloro or dichloro derivatives thereof are added to the reaction product.

In a third known process the reaction of ethylene with chlorine is carried out at temperatures from 75° to 200° C. and under pressures from 1 to 15 bar, and part of the liquid reaction mixture is removed and is divided into two streams. As much 1,2-dichloroethane as is subsequently formed by the reaction of ethylene with chlorine is vaporized from one of the two streams. The vaporized 1,2-dichloroethane is rectified, and the non-vaporized product is recycled to the reaction zone. The other of the two streams is passed through a heat exchanger. Some of the heat transferred therein is used for the distillation of the 1,2-dichloroethane, it being possible to mix in 1,2-dichloroethane produced by other means. Higher-boiling products are removed from the bottom product of the column.

The two processes first mentioned have the disadvantage of impurities of lower volatility than 1,2-dichloroethane remaining in the system, which results in difficulties. In some cases it is necessary to add extraneous substances (cresols or chlorination products thereof). All three processes are not suitable for purifying aqueous 1,2-dichloroethane from oxychlorination. Although the addition of 1,2-dichloroethane of a different origin is possible in principle in the third process, this addition is effected in the direct chlorination reactor, in which water is undesirable on account of corrosion problems.

In a further process for the distillation of 1,2-dichloroethane it is known to subject the 1,2-dichloroethane to a pressure of more than one atmosphere (absolute) in a column in which the high-boilers are removed, by adjusting the pressure at the head of the column, to raise the vaporous 1,2-dichloroethane taken off from the column, in a compressor, to a pressure at least 0.5 kg/cm$^2$ higher than the pressure at the head of the column and to a temperature which is at least 7° C. higher than the head temperature of the column, and to obtain heat from this gas. The pressure at the head of the column is thus adjusted to a value between 0.5 and 1.5 kg/cm$^2$ higher than normal atmospheric pressure, and the pressure is raised in the compressor to values between 0.5 and 2.0 kg/cm$^2$ higher than the pressure at the head of the column. It is recommended not to allow the pressure in the column to rise to a value more than 1.5 kg/cm$^2$ higher than normal atmospheric pressure, and, correspondingly, to operate the column at an elevated temperature, since this accelerates the decomposition of the high-boiling substances in the 1,2-dichloroethane, whereby problems are caused in the purification of this substance.

The disadvantage of this process is the necessity of using expensive compressors, which, as a rule, are operated not directly by means of heat energy but by means of more expensive electrical energy.

A process has now been found which does not have the disadvantages described above and which can be carried out without increased capital costs in equipment which is usually available, with low reconstruction costs. This process for the purification of 1,2-dichloroethane containing less than 3% by weight of substances having a boiling point under atmospheric pressure higher than 1,2-dichloroethane, by distillation in a first column with continuous admission of impure 1,2-dichloroethane, and by the introduction of the bottom product from this column into a second distillation column operating under a lower pressure than the first column, comprises regulating the discharge of the bottom product from the first column in such a way that this product contains not more than 7% by weight of substances boiling above 1,2-dichloroethane, adjusting the head temperature in the first column to 125° to 180° C. and taking off vaporous 1,2-dichloroethane at the head of this column, passing it through one or more heat exchangers which serve(s) to heat up product streams containing 1,2-dichloroethane and then recycling part of it in liquid form to the first column mentioned and removing part of it as a purified product and using the latter for further purposes.

It has been found that, in contrast with the known state of the art, it is possible to operate the column in which 1,2-dichloroethane is separated from higher-boiling substances at comparatively high temperatures and corresponding pressures without difficulties, if care is taken that the bottom product from the column does not contain more than, at the most, 7% by weight, preferably 2 to 5% by weight, of substances boiling above 1,2-dichloroethane. The 1,2-dichloroethane fed to the column should contain less than 3% by weight of higher-boiling substances; if this is not the case, it is generally no longer possible to operate the column economically. Preferably the feed product contains 0.1 to 1% by weight of substances boiling above 1,2-dichloroetchane The bottom product from the said column, containing not more than 7% by weight of substances boiling above 1,2-dichloroethane, is fed to a second distillation column which is advantageously operated under a pressure of 5 to 40 kPa and in which further 1,2-dichloroethane is removed by distillation from the bottom product from the first column. Above a pressure of 40 kPa the removal of 1,2-dichloroethane is only partially successful; below a pressure of 5 kPa the outlay on equipment generally becomes too high and no longer bears any relation to the additional effect achieved thereby. It is preferable to operate at 8 to 30 kPa.

In a preferred embodiment of the process according to the invention, vaporous 1,2-dichloroethane originating from the reaction of ethylene with chlorine in the presence of a catalyst at 40° to 110° C. is fed to the column operated under a pressure of 5 to 40 kPa. Below 40° C. the recovery of heat is not of interest; above 110° C. there is a marked increase in the byproducts formed, so that losses of yield result and a higher outlay on purification becomes necessary. It is expedient to interpose a means of regulating the pressure between the vessel in which the reaction takes place and the column. The reaction of ethylene with chlorine is carried out by known processes in the presence of catalytic amounts of a Lewis acid, for example iron-(III) chloride. It is advantageous to use a catalyst system such as is described in European patent application No. 082,342-A2.

In a further advantageous embodiment of the process according to the invention, vaporous 1,2-dichloroethane originating, as described above, from the reaction of ethylene with chlorine at 40° to 110° C. in the presence of a catalyst is compressed to the pressure prevailing in the column operated with not more than 7% by weight of high-boilers in the bottom product, and is fed into this column.

The column in which the bottom product contains not more than 7% by weight of substances boiling above 1,2-dichloroethane (described below as "high-boilers") is operated at a head temperature of 125° 180° C. Below 125° C. the possible use of the 1,2-dichloroethane removed in vaporous form from the column is considerably limited, so that it is then more advantageous to compress a product of this type in accordance with the state of the art to a higher pressure and a higher temperature. If the column is operated at a head temperature above 180° C., difficulties caused by decomposition products occur to an increasing extent. It is advantageous to adjust the head temperature of the column to 130° to 160° C., in particular to 135° to 155° C.

The column described in the previous paragraph is operated with a continuous feed of impure 1,2-dichloroethane. This can be of various origins. For example, it can originate from a direct chlorination of ethylene from which the catalyst has been extracted by washing in the usual manner, if the reaction product has been taken off in liquid form, and the washed crude product has been separated in a column from water and substances boiling below 1,2-dichloroethane. It can also originate from an oxychlorination, having been previously purified, as described, by the removal of water and substances boiling below 1,2-dichloroethane. The 1,2-dichloroethane can also originate from thermal cracking, having not been reacted and having been obtained from the secondary products of the cracking after the separation of the hydrogen chloride and of the vinyl chloride formed. A product of this type is expediently subjected to a preliminary purification, for example by the addition of chlorine, whereby undesirable byproducts are chlorinated and hence rendered more readily removable. Chlorination of this type is expediently carried out at temperatures from 30° to 60° C., since at higher temperatures the 1,2-dichloroethane is also attacked and undesirable losses of product, as well as further side reactions, take place. It is advantageous in this respect to divide the recovered 1,2-dichloroethane, which has been cooled to a temperature within the range indicated above, in a ratio of 1:2 to 6, the smaller fraction being either fed to the direct chlorination of ethylene or, if the latter reaction is carried out with an unsuitable catalyst, reacted on its own with chlorine in the presence of iron-(III) chloride. The larger fraction of the recovered 1,2-dichloroethane is advantageously treated with chlorine without the addition of a catalyst and, after a certain treatment period, fed directly into the column operated at 125° to 180° C. The amount of added chlorine is such that the product contains less than 20 parts of chlorine per 1,000,000 parts of 1,2-dichloroethane before entering the column. At a ratio of 1:>6, the benzene content in the pure 1,2-dichloroethane generally becomes too high. Although a ratio of 1:<2 is possible, it generally requires an excessively high outlay on chlorination.

Vaporous 1,2-dichloroethane is taken off at the head of the column operated at 125° to 180° C. and is passed through one or more heat exchangers which serve(s) to heat up the product streams containing 1,2-dichloroethane. The following are advantageous possible means of using this vaporous 1,2-dichloroethane:

(a) heating the bottom product of a column in which water and/or other substances having a boiling point lower than 1,2-dichloroethane under atmospheric pressure are removed from the latter by distillation;

(b) heating the bottom product of the column which is operated under a pressure of 5 to 40 kPa and in which 1,2-dichloroethane is separated as completely as possible from the high-boilers;

(c) heating the 1,2-dichloroethane which did not react in the thermal cracking and has previously been chlorinated, and which is then fed directly into the column operated at 125° to 180° C.;

(d) heating the liquid 1,2-dichloroethane which has been condensed and cooled below its condensation temperature and which has been obtained after passing through the heat exchangers of the processes mentioned under (a) to (c) or further heating processes, before said liquid 1,2-dichloroethane is recycled into the column operated at 125° to 180° C.; and (e) heating the condensed, liquid 1,2-dichloroethane which has passed through at least one heat exchanger for the heating processes mentioned under (a) to (c) or further heating processes, after which the liquid 1,2-dichloroethane thus heated is fed to the thermal cracking reaction for the production of vinyl chloride.

For reasons of operating safety and in order to achieve the most favorable combined utilization of energy possible, it is advantageous to provide in each case, in addition to the heat exchangers which are heated by vaporous 1,2-dichloroethane and serve to heat the bottom products of various columns, also a second heat exchanger which can be heated in the customary manner by steam. It is also advantageous to control the level of the liquid 1,2-dichloroethane in the heat exchangers and to link this to a means of controlling the pressure at the head of the column operated at 125° to 180° C.

The process according to the invention makes possible a good utilization of the energy to be used for the purification of 1,2-dichloroethane. A particular advantage of the process is that it can be carried out in devices which are available in most cases, without major reconstruction or capital costs for new equipment.

BRIEF DESCRIPTION OF THE DRAWING

FIG. 1 is a schematic diagram of a system which may be used to carry out a process according to the invention.

The following examples are intended to illustrate the invention in greater detail:

FIG. 1 shows in diagram form a device suitable for carrying out the process according to the invention: a distillation column (1), suitable for pressures up to 1500 kPa, is connected to two heat exchangers (2) and (2a) which can be operated by steam. The bottom product from the column is passed via the line (3) into the column (4) suitable for vacuum operation. The latter is in turn connected to two heat exchangers, one (5) of which can be operated by steam. Hot 1,2-dichloroethane gas which has been taken off at the top of column (1) is passed into the other of the two heat exchangers (6) either via the line (7), through a cross heat exchanger (8) or directly via the line (9). The condensate from the heat exchanger (6) is passed into a stock tank (13) for pure 1,2-dichloroethane either via lines (10) and (11) through the cross heat exchanger (8) or directly via line (12). From this stock tank, part of the product is recycled via line (14) to column (1); the remainder passes via line (15) to a further storage vessel for pure 1,2-dichloroethane (16), from which it is fed to thermal cracking (18) via line (17).

The products from thermal cracking are worked up in a combination (19) of equipment not illustrated here in detail. The vinyl chloride is passed to a collecting vessel (20) and is used for further purposes from there. The hydrogen chloride passes via line (21) to an oxychlorination apparatus (22) into which ethylene and oxygen, in the shape of air, are also fed.

The impure 1,2-dichloroethane which has not reacted in the thermal cracking reaction passes from the working up unit (19) via line (23) to a cooler (24), where it is cooled to about 40° to 60° C. It leaves the cooler via line (25) and is split into two part streams. Chlorine is added to the larger of the two part streams in line (26). After a certain distance, which is required for the complete reaction of the chlorine, the product passes through a heat exchanger (27), and the heated product is fed via line (28) to column (1). A part stream of the hot 1,2-dichloroethane gas withdrawn at the head of column (1) is taken off as a side stream and is passed via line (29) and, after renewed subdivision, via line (30) through the heat exchanger (27), where it heats up the previously purified recycled 1,2-dichloroethane from the working up unit (19) of the product from thermal cracking. The condensed liquid 1,2-dichloroethane is passed via lines (31) and (11) or (12) into the stock tank (13) for 1,2-dichloroethane.

The smaller fraction of the cooled recycled 1,2-dichloroethane from line (25) can optionally be fed via line (33) to a vessel (34) in which it is treated with chlorine and a catalyst, for example $FeCl_3$. The liquid 1,2-dichloroethane discharged from this vessel, and treated with chlorine, is passed via line (35) and a washer (36) to the storage vessel (37) for wet 1,2-dichloroethane. 1,2-dichloroethane from oxychlorination (22), which also contains water, is passed via line (38) to the same storage vessel. Column (40) is fed via line (39) from the storage vessel (37). An azeotropic mixture of water and 1,2-dichloroethane and also the low-boilers are taken off at the head of this column via line (41). The bottom product from column (40) is fed via line (42) to column (1). Two heat exchangers, one of which (43) is fed with steam, are used to heat the bottom of column (40). Hot 1,2-dichloroethane vapor which has been taken off from the head of column (1) is passed into the other heat exchanger (44) via lines (29) and (45). The condensed 1,2-dichloroethane flows via lines (46) and either (11) or (12) to the pure 1,2-dichloroethane tank (13).

If separate chlorination of the recycled 1,2-dichloroethane is not necessary, the smaller fraction of the product arriving via line (25) is passed via line (47) to tank (48), in which ethylene is reacted with chlorine in the presence of a catalyst in liquid 1,2-dichloroethane. The reaction mixture is cooled via a ring line (49) and a cooler (50).

Vaporous 1,2-dichloroethane can be taken off via a pressure controller (48a) at the top of tank (48) and can either be fed via lines (51) and (52) to column (4) or can be brought to an appropriate pressure via line (51), the compressor (53) and line (54) and fed into column (1).

The bottom product of column (4) leaves the latter via line (55). It contains essentially the high-boilers. At the head of column (4), vaporous 1,2-dichloroethane is taken off via line (56), condensed in the condenser (57) and in part fed back to column (4) via line (58), the remaining part being passed via lines (32), (31), (11) or (12) to the pure 1,2-dichloroethane tank (13). The level controllers (6a) and (44a) of heat exchangers (6) and (44) are controlled by the pressure controller (1a) of column (1).

If required, other substances, preferably containing 1,2-dichloroethane, can be heated by means of the hot vaporous 1,2-dichloroethane taken off from the head of column (1) via lines (29) and (59). Similarly, if required, part of the liquid from the cooling circuit (49) for the reaction of ethylene with chlorine can be taken off via line (60) and fed to washer (36).

EXAMPLE 1

An apparatus according to FIG. 1 is used, but the following parts are not utilized: line (33), vessel (34), line (35), pressure controller (48a), lines (51), (52) and (54) and compressor (53). The 1,2-dichloroethane produced from ethylene and chlorine in vessel (48) is passed via line (60) to washer (36). The smaller fraction of the recycled 1,2-dichloroethane is fed via line (47) to vessel (48).

2.87 parts by weight of 1,2-dichloroethane are produced in the direct chlorination reaction (vessel 48) using an iron-(III) chloride catalyst at normal atmospheric pressure and 50°C. The 1,2-dichloroethane contains as impurities 0.098% by weight of ethyl chloride as a low-boiler and 0.205% by weight of 1,1,2-trichloroethane as a high-boiler (the percentages relate to the crude product). 1,2-Dichloroethane is taken off as a liquid via line (60) and is washed with water in vessel (38). At the same time, 1.08 parts by weight of 1,2-dichloroethane which did not react in the thermal cracking reaction are fed via line (47) to the direct chlorination (48).

2.7 parts by weight of 1,2-dichloroethane are produced in vessel (22) from hydrogen chloride, ethylene and atmospheric oxygen. This product contains 99.2% by weight of 1,2-dichloroethane (the remainder is composed of substances boiling below and above 1,2-dichloroethane) and is passed to vessel (37). The products from direct chlorination (48) and oxychlorination (22) are combined there and are freed from water and low-boilers in column (40). The bottom of this column is heated by means of steam in heat exchanger (43) and by means of vaporous 1,2-dichloroethane in heat exchanger (44). The column operates under normal atmospheric pressure, with a head temperature of 75° C.

The bottom product from column (40) is fed to column (1) and is rectified there at a head temperature of 130° C. and a pressure of 364 kPa at the head of the column. 1.9 parts by weight of a product containing, in addition to 1,2-dichloroethane, 3.6% by weight of substances boiling above 1,2-dichloroethane are taken off from the bottom of column (1). 10.65 parts by weight of hot, vaporous 1,2-dichloroethane are taken off at the head of column (1) and are passed to the heat exchangers described earlier and later in the text, in each of which it heats up a product containing 1,2-dichloroethane. The bottom of column (1) is heated by means of steam. The bottom product is passed to column (4) and is distilled there at a head temperature of 45° C. and a pressure of 25 kPa at the head of the column. The bottom of column (4) is heated in part with steam and in part with vaporous 1,2-dichloroethane from column (1).

1,2-Dichloroethane having a purity of 99.6% is subjected to thermal cracking in a cracking furnace operated in accordance with a known process, and is then cooled and worked up by distillation. The hydrogen chloride separated from the products of cracking in the course of this is reacted with ethylene and air in the oxychlorination system (vessel 22) described earlier in the text, and the vinyl chloride which is also separated off is fed to the storage vessel (20) for further use. The unreacted 1,2-dichloroethane obtained as the bottom product from the distillation, containing byproducts as impurities, is first cooled to 40° C. and is then divided in a ratio of 3:1. The smaller part (1.08 parts by weight) of the divided amount is fed, as described above, to direct chlorination in vessel (48). The larger part (3.24 parts by weight) is treated with chlorine in an amount such that the chlorine content of the product before entering column (1) is below 0.002% by weight. For a distance after the addition of chlorine, the 1,2-dichloroethane thus treated is heated in heat exchanger (27) with hot, vaporous 1,2-dichloroethane from column (1) and is fed to this column via line (28). The combined streams of condensed, liquid 1,2-dichloroethane from heat exchangers (6), (44) and (27), and also from the cooler (57) are passed, as can be seen from the diagram in FIG. 1, via line (11) through the cross heat exchanger (8) and are heated in the latter with hot 1,2-dichloroethane gas from column (1). The 1,2-dichloroethane used for heating in this case, which remains essentially vaporous, then passes through heat exchanger (6), which heats the bottom of column (4). The ratio in which the 1,2-dichloroethane which does not react in the thermal cracking reaction is divided is so regulated that the product in vessel (13) contains less than 0.1% by weight of benzene. If this figure increases, the fraction of 1,2-dichloroethane which is fed via line (47) to direct chlorination (48) is increased at the expense of the fraction passing via line (26).

The pure 1,2-dichloroethane flows from vessel (13) at a temperature of 125° C. via line (15) to vessel (16).

A specific energy consumption of 151 kJ per kilogram of pure 1,2-dichloroethane is recorded in this process.

COMPARISON TEST A

The procedure followed is as described in Example 1, but heat exchangers (6), (44) and (27) are heated with steam. Column (1) is operated at a temperature of 90° C. and a pressure of 120 kPa at the head of the column. The top product from column (1) is cooled in a condenser (not shown in FIG. 1) until it condenses and is then passed to vessel (13), from which it flows at a temperature of 70° C. via line (15) to vessel (16). A specific energy consumption of 867 kJ/kg of pure 1,2-dichloroethane is determined in this process.

EXAMPLE 2

An apparatus according to FIG. 1 is used, but the following sections of apparatus are not used: lines (47), (52) and (60). 2.86 parts of 1,2-dichloroethane containing, as impurities, 0.005% by weight of ethyl chloride as a low-boiler and 0.103% by weight of 1,1,2-trichloroethane as a high-boiler is produced by reacting ethylene with chlorine in vessel (48) at 97° C. and a pressure of 150 kPa, using a catalyst containing iron, as specified in German Offenlegungsschrift No. 3,148,450. This product is fed in the form of vapor via line (51) to the turbocompressor (53), in which it is compressed from 150 kPa to a pressure of 450 kPa and is heated to a temperature of 140° C., and is fed via line (54) to column (1).

The thermal cracking of the 1,2-dichloroethane and the working up of the products from cracking are carried out as described in Example 1. The impure 1,2-dichloroethane which has not reacted in the cracking is cooled to 40° C. and again divided in a ratio of 1:3. The smaller fraction (1.08 parts by weight) flows via line (33) to vessel (34) where it is treated with chlorine in the presence of iron-(III) chloride. The chlorinated product flows via line (35) to the water washer (36) and from there to the storage vessel (37), where it is combined with the stream of 1,2-dichloroethane arriving via line (38) from oxychlorination (22). The combined streams are then separated, as described in Example 1, from water and low-boilers in column (40), and the bottom product from this column fed to column (1).

The larger fraction of the impure 1,2-dichloroethane which has not reacted in the thermal cracking (3.24 parts by weight) is treated with chlorine, heated and fed to column (1), as described in Example 1.

Column (1) is operated at a head temperature of 135° C. and a pressure of 400 kPa at the head of the column. 10.65 parts by weight of vaporous 1,2-dichloroethane are taken off at the head of the column and are passed to heat exchangers (27) and (44) and also via the cross heat exchanger (8) to heat exchanger (6), as described in Example 1. The liquid, condensed 1,2-dichloroethane is recycled from the heat exchangers to vessel (13) as described in Example 1.

1.9 parts by weight of a product containing, in addition to 1,2-dichloroethane, 3.5% by weight of substances boiling above 1,2-dichloroethane is taken off from the bottom of column (1). This product is fed to column (4) and is distilled there at a head temperature of 40° C. and a pressure of 20 kPa at the head of the column. The bottom product and the top product from this column are treated as described in Example 1.

A specific energy consumption of 35 kJ/kg of pure 1,2-dichloroethane is recorded.

EXAMPLE 3

An apparatus as described in Example 1 is used, the following parts of the apparatus not being utilized: lines (47) and (60), compressor (53) and line (54). 2.86 parts by weight of 1,2-dichloroethane are produced by reacting ethylene with chlorine at 97° C. and a pressure of 150 kPa in vessel (48), using a catalyst containing iron as specified in German Offenlegungsschrift No. 3,148,450. The 1,2-dichloroethane removed in vaporous form via line (51) contains, as impurities, 0.0049% by weight of ethyl chloride as a low-boiler and 0.097% by weight of 1,1,2-trichloroethane as a high-boiler (all percent by weight data relate to the impure product). After passing through a pressure-reducing valve, the 1,2-dichloroethane conveyed in line (51) is introduced via line (52) into column (4), which is operated at a head temperature of 50° C. and a pressure of 30 kPa at the head of the column.

Column (1) is operated at a head temperature of 160° C. and a pressure of 650 kPa at the head of the column. 6.9 parts by weight of vaporous 1,2-dichloroethane are taken off at the head of column (1) and are used for further purposes as described in Example 1. 1.9 parts by weight of a product containing, in addition to 1,2-dichloroethane, 3.4% by weight of substances boiling above 1,2-dichloroethane is taken off from the bottom of the column (1) and is introduced into column (4).

The impure 1,2-dichloroethane which has not reacted in the thermal cracking is treated further as described in Example 2. In other respects the procedure followed in Example 3 is evident from Example 1 or from the explanation relating to FIG. 1.

A specific energy consumption of 101 kJ/kg of pure 1,2-dichloroethane is recorded.

In all the examples, and also in the comparison test, all the figures of parts by weight relate to the same time unit.

We claim:

1. A process for the purificaition of 1,2-dichloroethane containing less than 3% by weight of substances having a boiling point at atmospheric pressure higher than 1,2-dichloroethane, which comprises distilling 1,2-dichloroethane in a first column which is continuously fed with impure 1,2-dichloroethane; discharging a bottom product of the first column and feeding said bottom product of the first column to a second column which operates at lower pressure than the first column; regulating said bottom product of the first column to a content of not more than 7% by weight of substances boiling above 1,2-dichloroethane; discharging a bottom product of the second column containing essentially the substances having a boiling point at atmospheric pressure higher than 1,2-dichloroethane; distilling a head product of the first column and a head product of the second column containing essentially vaporous 1,2-dichloroethane; operating the first column at a head temperature of 125° to 180° C.; cooling the vaporous 1,2-dichloroethane which is distilled as the head product of the first column in at least one heat exchanger to heat a 1,2-dichloroethane containing product and to provide a condensate of the vaporous 1,2-dichloroethane; and feeding a portion of said condensate from said heat exchanger to the first column and feeding the remaining portion to a thermal cracking.

2. The process as claimed in claim 1, further comprising operating the second column at a pressure of 5 to 40 kPa and wherein the bottom product of the second column is heated in a heat exchanger with the vaporous 1,2-dichloroethane which is distilled as the head product of the first column.

3. The process as claimed in claim 1, further comprising cooling the vaporous 1,2-dichloroethane which is distilled as the head product of the first column in a heat exchanger to heat a bottom product of a third column in which water and other substances having a boiling point lower than 1,2-dichloroethane at atmospheric pressure are distilled as a heat product of the third column from impure 1,2-dichloroethane.

4. The process as claimed in claim 1, further comprising feeding unreacted 1,2-dichloroethane from the thermal cracking to a working-up unit; cooling the unreacted 1,2-dichloroethane to about 40° to 60° C.; adding chlorine to the cooled 1,2-dichloroethane; heating said chlorine and cooled unreacted 1,2-dichloroethane in a heat exchanger with the vaporous 1,2-dichloroethane which is distilled as the head product of the first column; and then feeding said heated unreacted 1,2-dichloroethane to the first column.

5. The process as claimed in claim 1, further comprising feeding the vaporous 1,2-dichloroethane which is distilled as the head product of the first column first through a cross heat exchanger and then into a second heat exchanger in which the bottom product to the second column is heated and a condensate of the vaporous 1,2-dichloroethane is formed; heating the condensate from the second heat exchanger in the cross heat exchanger; and then feeding a portion of said condensate to the first column and feeding the remaining portion to the thermal cracking reaction for the production of vinyl chloride.

* * * * *